United States Patent [19]

Kisida et al.

[11] Patent Number: 5,137,907

[45] Date of Patent: Aug. 11, 1992

[54] 1-(3-(4-(3,5-DIFLUOROPHENOXY) PHENOXY) PROPYL) - PYRAZOLE, AND ITS PRODUCTION AND USE

[75] Inventors: Hirosi Kisida, Takarazuka; Sumio Nishida, Toyonaka; Akira Shuto, Takarazuka; Makoto Hatakoshi, Toyonaka, all of Japan

[73] Assignee: Sumitomo Chemical Company, Limited, Osaka, Japan

[21] Appl. No.: 724,769

[22] Filed: Jul. 2, 1991

Related U.S. Application Data

[63] Continuation-in-part of Ser. No. 450,925, Dec. 14, 1989, abandoned.

[30] Foreign Application Priority Data

Dec. 27, 1988 [JP] Japan .................. 63-331076

[51] Int. Cl.$^5$ .................. A61K 31/415; C07D 231/10
[52] U.S. Cl. .................. 514/406; 548/378
[58] Field of Search .................. 548/378; 514/406

[56] References Cited

U.S. PATENT DOCUMENTS

| | | | |
|---|---|---|---|
| 3,190,888 | 6/1965 | Wolf et al. | 548/378 |
| 3,904,662 | 9/1975 | Henrick et al. | 548/373 |
| 4,870,174 | 9/1989 | Paradies | 548/378 |
| 4,874,850 | 10/1989 | Paradies | 548/378 |
| 4,877,883 | 10/1989 | Paradies | 548/378 |
| 4,882,435 | 11/1989 | Paradies | 548/378 |
| 4,894,454 | 1/1990 | Paradies | 548/378 |
| 4,943,586 | 7/1990 | Bowers et al. | 548/373 |
| 4,965,357 | 10/1990 | Paradies | 548/378 |
| 4,999,435 | 3/1991 | Paradies | 548/378 |
| 5,045,530 | 9/1991 | Paradies | 548/378 |

FOREIGN PATENT DOCUMENTS

| | | |
|---|---|---|
| 1231945 | 1/1988 | Canada . |
| 0069848 | 1/1983 | European Pat. Off. . |
| 0262344 | 4/1988 | European Pat. Off. . |
| 0287959 | 4/1988 | European Pat. Off. . |
| 9006678 | 6/1990 | World Int. Prop. O. . |

OTHER PUBLICATIONS

Chem. Abs. 111:205323q (1989).
Chem. Abs. 91:74523y (1979).
Chem. Abs. 101:8350p (1984).
Chem. Abs. 107:23735k (1987).
Chem. Abs. 108:134239s (1988).
Chem. Abs. 109:50259f (1988).

*Primary Examiner*—Johann Richter
*Attorney, Agent, or Firm*—Birch, Stewart, Kolasch & Birch

[57] ABSTRACT

A pyrazole compound of the formula:

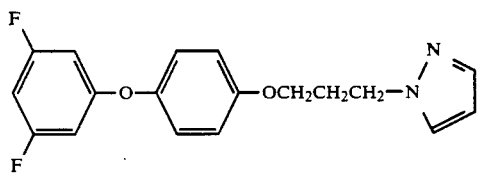

which is useful as an insect pesticide.

3 Claims, No Drawings

1-(3-(4-(3,5-DIFLUOROPHENOXY) PHENOXY) PROPYL) - PYRAZOLE, AND ITS PRODUCTION AND USE

This is a continuation-in-part application of our co-pending application Ser. No. 07/450,925 filed Dec. 14, 1989, now abandoned.

The present invention relates to a pyrazole compound, i.e. 1-{3-[4-(3,5-difluorophenoxy)phenoxy]-propyl}pyrazole, and its production and use.

Organophosphorus insecticides, organochlorinated insecticides, carbamate insecticides, etc. have made a great contribution in prevention and extermination of insect pests. Some of these insecticides, however, produce a high toxicity. Further, their residual effect causes sometimes unfavorable abnormality in the ecosystem of living things. Furthermore, resistance to those insecticides is noticed in house flies, planthoppers, leafhoppers, rice borers, etc.

As the insect pesticide having a juvenile hormone-like activity, there is known "methoprene" (U.S. Pat. No. 3,904,662). Further, Canadian patent 1,231,945 and EP-A1-0287959 disclose certain compounds having a juvenile hormone-like activity. However, the insect pesticidal activity of those compounds is not always satisfactory.

As a result of the extensive study, it has now been found that 1-{3-[4-(3,5-difluorophenoxy)phenoxy]-propyl}pyrazole, exerts a noticeable juvenile hormone-like activity and produces a remarkable insect pesticidal effect against insect pests belonging to Diptera, Hemiptera, Coleoptera, Lepidoptera, Orthoptera, Blattaria, Thysanoptera, Siphonaptera, Isoptera, etc. in agricultural fields, forest lands, granaries, stored products, sanitary facilities, etc. at low concentrations. This invention is based on the above finding.

The pyrazole compound of the invention has the following formula:

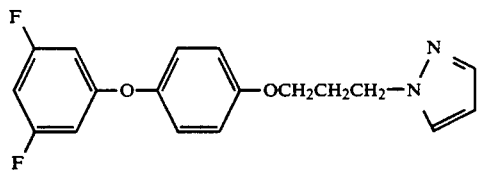
(I)

The pyrazole compound (I) can be produced, for instance, by reacting a compound of the formula:

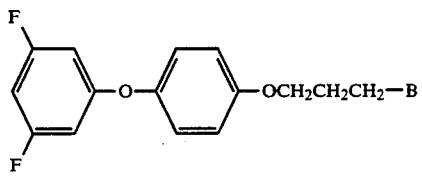
(II)

wherein B is a halogen atom (e.g. chlorine, bromine), a mesyloxy group or a tosyloxy group with a compound of the formula:

(III)

in the presence of an acid-eliminating agent.

The above reaction may be carried out in the presence or absence of an inert solvent, of which preferred examples are dimethylformamide, dimethylsulfoxide, tetrahydrofuran, toluene, dimethoxyethane, dimethylacetamide, etc. As the acid-eliminating agent, there may be employed an alkali metal, an alkali metal hydride, an alkali metal amide, an alkali metal hydroxide, an alkali metal carbonate, an organic base (e.g. 4-dimethylaminopyridine), etc. For acceleration of the reaction, a phase transfer catalyst such as benzyltriethylammonium chloride, tetra-n-butylammonium bromide or tris(3,6-dioxaheptyl)amine may be present in the reaction. In this instance, water can be used as the reaction medium.

The reaction is normally achieved at a temperature of about $-30°$ C. to $200°$ C., preferably of about $0°$ C. to $110°$ C., for about a period of 0.5 to 30 hours. The molar ratio of the compounds (II) and (III) is usually about 1:0.1–10 moles, preferably about 1:0.8–1.2 moles.

Upon completion of the reaction, the reaction mixture is subjected to ordinary post treatment such as extraction with an organic solvent and concentration. When desired, purification by chromatography, distillation, recrystallization or the like may be carried out.

The compound (II) as the starting material in the above process can be easily produced from appropriate commercial products by various conventional procedures, of which an example is shown below:

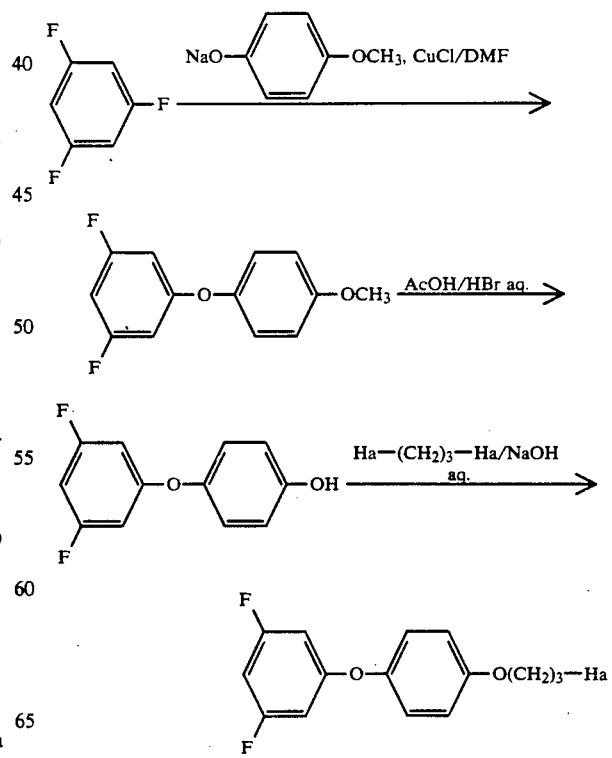

wherein Ha is a halogen atom (e.g. chlorine, bromine).

A practical and presently preferred embodiment for preparation of the pyrazole compound (I) is illustratively shown in the following Synthesis Example.

SYNTHESIS EXAMPLE 1

To a mixture of anhydrous N,N-dimethylformamide (30 ml) and sodium hydride (60% oil suspension; 0.70 g), pyrazole (1.19 g) was added, and the resultant mixture was stirred for 30 minutes. A solution of 3-[4-(3,5-difluorophenoxy)phenoxy]propyl bromide (5.00 g) in anhydrous N,N-dimethylformamide (20 ml) was dropwise added thereto, followed by stirring at room temperature for 5 hours. The reaction mixture was diluted with ethyl acetate (200 ml), washed with a saturated aqueous ammonium chloride solution two times, dried over anhydrous magnesium sulfate and concentrated under reduced pressure. The oily substance thus obtained was subjected to column chromatography to give 4.20 g of 1-{3-[4-(3,5-difluorophenoxy)phenoxy]-propyl}pyrazole as a colorless oil. $n_D^{23.5}$ 1.5746.

Examples of the insect pests against which the pyrazole compound (I) exhibits a controlling effect are as follows:

Hemiptera:

Planthoppers such as brown planthopper (*Nilaparvata lugens*), white-backed rice planthopper (*Sogatella furcifera*) and small brown planthopper (*Laodelphax striatellus*); leafhoppers such as green rice leafhopper (*Nephotettix cinticeps*), *Nephotettix virescense*, *Nephotettix nigropictus*, zig-zag rice leafhopper (*Recilia dorsalis*), tea green leafhopper (*Empoasca onukii*) and grape leafhopper (*Arboridia apicalis*); aphids such as cotton aphid (*Aphis gossypii*) and green peach aphid (*Myzus persicae*); bugs; whiteflies (*Aleyrodiae*) such as sweet potato whitefly (*Bemisia tabaci*) and greenhouse whitefly (*Trialeurodes vaporariorum*); scales; mealy bugs; lace bugs (Tingidae); psyllids (Psyllidae), etc.

Lepidoptera:

Pyralid moths (Pyralidae) such as rice stem borer (*Chilo suppressalis*), rice leafroller (*Cnaphalocrocis medinalis*) and Indian meal moth (*Plodia interpunctella*); Noctuidae such as tobacco curworm (*Spodoptera litura*), rice armyworm (*Pseudaletia separate*), cabbage armyworm (*Mamestra brassicae*) and beet semi-looper (*Autographa nigrisigna*); Agrothis spp. such as turnip cutworm (*Agrothis segetum*) and black cutworm (*Agrothis ipsilon*); Heliothis spp.; Pieridae such as common cabbageworm (*Pieris rapae crucivora*); tortricid moths (Tortricidae) such as Adoxophyes spp. and Grapholita spp.; Carposinidae such as lyonetiid moths (Lyonetiidae), leafblotch miners (Gracillariidae), gelechiid moths (Gelechiidae) and tussock moths (Lymantriidae); diamondback moth (*Plutella xylostella*), clothes moths (Tineidae), casemaking clothes moth (*Tinea translucens*) and webbing clothes moth (*Tineola bisselliella*), etc.

Diptera:,

Mosquitos (Calicidae) such as common mosquito (*Culex pipiens pallens*) and *Culex tritaeniorhynchus*; Aedes spp. such as *Aedes aegypti* and *Aedes albopictus*; Anopheles spp. such as *Anopheles sinensis*; midges (Chironomidae); Muscidae such as housefly (*Musca domestica*) and false stablefly (*Muscina stabulans*); Calliphoridae; Sarcophagidae; lesser housefly (*Fannia canicularis*); anthomyiid flies (Anthomyiidae) such as seedcorn maggot (*Delia platura*) and onion maggot (*Delia antique*); fruit flies (Tephritidae); shore flies (Ephydridae); small fruit flies (Drosophilidae); moth flies (Psychodidae); black flies (Simuliidae); Tabanidae; stable flies (Stomoxyidae); etc.

Coleoptera:

Leaf beetles (Chrysomelidae) such as cucurbit beetle (*Aulacophora femoralis*), striped flea beetles (*Phyllotrata striolata*), western corn rootworm (*Diabrotica virgifora*) and southern corn root worm (*Diabrotica undecimpunctata*); scarabs (Scarabaeidae) such as cupreous chafer (*Anomala cuprea*) and soybeen beetle (*Anomala rufocuprea*); weevils (Cureulionidae) such as maize weevil (*Sitophilus zeamais*), rice water weevil (*Lissorhoptrus oryzophilus*) and adzuki bean weevil (*Callosobruchys chineneis*), etc.; darkling beetles (Tenebrionidae) such as yellow mealworm (*Tenebrio moliter*) and red fluor beetles (*Tribolium castaneum*); Anobiidae; Coccinellidae such as twenty-eight-spotted ladybirds (*Epilachna vigintioctopunctata*); powderpost beetles (Lyctidae); false powderpost beetles (Bostrychidae); Cerambysidae, etc.

Dictyoptera:

Blattellidae such as German cockroach (*Blattella germanica*); Blattidae such as smokybrown cockroach (*Periplaneta fuliginosa*), American cockroach (*Periplaneta americana*), brown cockroach (*Periplaneta brunnea*) and oriental cockroach (*Blatta orientalis*), etc.

Thysanoptera:

Thrips such as *Thrips palmi*, yellow tea thrips (*Scirtothrips dorsalis*) and flower thrips (*Thrips hawaiiensis*), etc.

Hymenoptera:

Ants (Formicidae); sawflies (Tenthredinidae) such as cabbage sawfly (*Athalia rosae ruficornis*), etc.

Orthoptera:

Mole crickets (Gryllotalpidae); grasshoppers (Acridiae), etc.

Aphaniptera:

*Purex irritans*, etc.

Anoplura:

*Pediculus humanus capitis, Phthirus pubis*, etc.

Isoptera:

*Reticulitermes speratus*, Formosan subterrauean termite (*Coptotermes formosanus*), etc.

In order to control the growth of the insect pests as above exemplified, the pyrazole compound (I) may be used as such, i.e. without admixing with any other component. For the practical usage, it is normally admixed with any additive(s) as conventionally used in the related art field to make insecticidal compositions. It may be thus admixed with solid carriers, liquid carriers, gaseous carriers, food substances, etc. When necessary or desired, the mixtures may be further supplemented with surfactants and/or other adjuvants to make insecticidal compositions in forms such as oil sprays, emulsifiable concentrates, wettable powders, flowable concentrates (e.g. water-based suspension formulations, water-based emulsion formulations), granules, dusts, aerosols, heat smoking formulatins (e.g. self-burning type smoking formulations, chemical reaction type smoking formulations, porous ceramic plate type smoking formulations), ULV formulations, poison baits, etc.

The insect pesticidal composition of the invention comprises the pyrazole compound (I) usually in a concentration of about 0.1 to 99.9% by weight, preferably about 2 to 80% by weight.

Examples of the solid carrier used for making the insect pesticidal composition include fine powders or granules, etc. of clays (e.g. kaolin clay, diatomaceous earth, synthetic hydrated silicon dioxide, bentonite, Fubasami clay, terra alba, etc.), talc, ceramics, other inorganic minerals (e.g. sericite, quartz; sulfur, activated carbon, calcium carbonate, hydrated silica, etc.), chemical fertilizers (e.g. ammonium sulfate, ammonium phosphate, ammonium nitrate, urea, ammonium chloride, etc.), etc. Examples of the liquid carrier include water, alcohols (e.g. methanol, ethanol, etc.), ketones (e.g. acetone), methyl ethyl ketone, etc.), aromatic hydrocarbons (e.g. benzene, toluene, xylene, ethylbenzene, methylnaphthalene, etc.), aliphatic hydrocarbons (e.g. hexane, cyclohexane, kerosene, gas oil, etc.), esters (e.g. ethyl acetate, butyl acetate, etc.), nitriles (e.g. acetonitrile, isobutyronitrile, etc.), ethers (e.g. diisopropyl ether, dioaxane, etc.), acid amides (e.g. N,N-dimethylformamide, N,N-dimethylacetamide, etc.), halogenated hydrocarbons (e.g. dichloromethane, trichloroethane, carbon tetrachloride, etc.), dimethylsulfoxide, vegetable oils (e.g. soybean oil, cotton seed oil), etc. Examples of the gaseous carrier, i.e. propellant, include freon gas, butane gas, LPG (liquefied petroleum gas), dimethyl ether, carbon dioxide, etc.

Examples of the surfactant include alkyl sulfates, alkyl sulfoates, alkylaryl sulfonates, alkyl aryl ethers and polyoxyethylene derivatives thereof, polyethylene glycol ether, polyvalent alcohol esters, sugar alcohol derivatives, etc.

Examples of the adjuvants such as binders, dispersing agents, etc. for formulations include casein, gelatin, polysaccharides (e.g. starch powders, gum arabic, cellulose derivatives, alginic acid, etc.), lignin derivatives, bentonite, sugars, synthetic water-soluble high molecular substances (e.g. polyvinyl alcohol, polyvinylpyrrolidone, polyacrylic acid, etc.). Examples of the stabilizer include PAP (acidic isopropyl phosphate), BHT (2,6-di-tert-butyl-4-methylphenol), BHA (mixture of 2-tert-butyl-4-methoxyphenol and 3-tert-butyl-4-methoxyphenol), vegetable oils, mineral oils, surfactants, fatty acids or esters thereof, and the like.

The base material for self-burning type smoking formulations includes, for example, heat-generating agents such as nitrates, nitrites, guanidine salts, potassium chlorate, nitrocellulose, ethyl cellulose, wood powders, etc.; pyrolysis-promoting agents such as alkali metal salts, alkaline earth metal salts, dichromates, chromates, etc.; oxygen-supplying agents such as potassium nitrate, etc.; burning-supporting agents such s melamine, wheat starch, etc.; extenders such as diatomaceous earth, etc.; and binders such as synthetic pastes, etc.

The base material for chemical reaction type smoking formulations includes, for example, heat-generating agents such as sulfides, polysulfides, hydrosulfides or salt hydrates of alkali metals, calcium oxide, etc.; catalyzing agents such as carbonaceous substances, iron carbide, activated clay, etc.; organic foaming agents such as azodicarbonamide, benzenesulfonyl hydrazide, dinitrosopentamethylenetetramine, polystyrene, polyurethane, etc.; fillers such as natural fiber pieces, synthetic fiber pieces, etc.

As the base material for poison baits, there are, for example, food components such as crop powders, essential vegetable oil, sugars, crystalline cellulose, etc.; antioxidants such as dibutylhydroxytoluene, nordihydroguaiaretic acid, etc.; preservatives such as dehydroacetic acid, etc.; mis-food preventing agents such as red pepper powders, etc.; incentive flavor such as cheese flavor, onion flavor, etc.

The flowable concentrates (water-based suspension formulations or water-based emulsion formulations) are generally obtained by finely dispersing about 1 to 75% of the active ingredient into water containing about 0.5 to 15% of a dispersing agent, about 0.1 to 10% of a suspending agent such as protective colloids (e.g. gelatin, casein, gum arabic, cellulose ethers, polyvinyl alcohols, etc) and thixotropic property-giving compounds (e.g. bentonite, aluminum magnesium sulicate, xanthane gum, polyacrylic acid, etc.) and about 0 to 10% of other auxiliary agent(s) (e.g. defoaming agents, anticorrosives, stabilizers, spreading agents, penetration auxiliaries, antifreezing agents, antibacterial agents, antimolding agents). It is also possible to obtain oil-based suspension formulations by replacing water by an oil which hardly dissolves the active compound.

The thus obtained formulations may be used as they are or after diluting with water, etc. Alternatively, the formulations may be used as admixture with other insecticides, nematocides, acaricides, fungicides, bacteriocides, herbicides, plant growth controllers, synergistic agents, fertilizers, soil conditioners, animal food, etc., or may also be used simultaneously with them, without mixing therewith.

The pyrazole compound (I) may be employed in conjunction with other insecticides and/or acaricides to enhance their insecticidal and/or pesticidal activity. Examples of the other insecticides and/or acaricides include organophosphorus compounds (e.g. fenitrothion (O,O-dimethyl O-(3-methyl-4-nitrophenyl)phosphorothioate), fenthion (O,O-dimethyl O-[3-methyl-4-(methylthio)phenyl]phosphorothioate), diazinon (O,O-diethyl-O-(2-isopropyl-6-methylpyrimidin-4-yl)phosphorothioate), chlorpyrifos (O,O-diethyl-O-(3,5,6-trichloro-2-pyridyl)phosphorothioate), acephate (O,S-dimethyl acetylphosphoramidothioate), methidathion (S-2,3-dihydro-5-methoxy-2-oxo-1,3,4-thiadiazol-3-ylmethyl O,O-dimethylphosphorodithioate), disulfoton (O,O-diethyl S-2-ethylthioethyl phosphorothioate), DDVP (2,2-dichlorovinyldimethylphosphate), sulprofos (O-ethyl O-4(methylthio)phenyl S-propyl phosphorodithioate), cyanophos (O-4-cyanophenyl O,O-dimethyl phosphorothioate), dioxabenzofos (2-methoxy-4H-1,3,2-benzodioxaphosphinine-2-sulphide), dimethoate (O,O-diethyl-S-(N-methylcarbamoylmethyl)dithiophosphate), phenthoate (ethyl 2-dimethoxyphosphinothioylthio(phenyl)acetate), malathion (diethyl (dimethoxyphosphinothioylthio)succinate), trichlorfon (dimethyl 2,2,2-trichloro-1-hydroxyethylphosphonate), azinphos-methyl (S-3,4-dihydro-4-oxo-1,2,3-benzotriazin-3-ylmethyl O,O-dimethylphosphoro-dithioate), monocrotophos (dimethyl (E)-1-methyl-2-(methylcarbamoyl)vinyl phosphate), etc.); carbamate derivatives (e.g. BPMC (2-sec-butylphenyl methylcarbamate), benfuracarb (ethyl N-[2,3-dihydro-2,2-dimethylbenzofuran-7-yloxycarbonyl (methyl)aminothio]-N-isopropyl-beta-alaninate), propoxur (2-isopropoxyphenyl N-methylcarbamate), carbosulfan (2,3-dihydro-2,2-dimethyl-7-benzo[b]furanyl N-methylcarbamate), carbaryl (1-naphthyl-N-methylcarbamate), methomyl (S-methyl-N-[(methylcarbamoyl)oxy]thioacetimidate), ethiofencarb (2-(ethylthiomethyl)phenyl methylcarbamate), aldicarb (2-methyl-2-(methylthio)propionaldehyde O-methylcarbamoyloxime), Oxamyl (N,N-dimethyl-2-methylcarbamoyloxyimino-2-(methylthio)acetamide), etc.); pyrethroides (e.g. ethofenprop (2-(4-ethoxyphenyl-2-methylpropyl-3-phenoxybenzylether), fenvalerate ((RS)-alpha-cyano-3-phenoxybenzyl (RS)-2-(4-chlorophenyl)-3-methylbutyrate), esfenvalerate ((S)-alpha-cyano-3-phenoxybenzyl (S)-2-(4-chlorophenyl)-3-methylbutyrate), fenpropathrin ((RS)- alpha-cyano-3-phenoxybenzyl 2,2,3,3-tetramethylcyclopropanecarboxylate), cypermethrin ((RS)-alpha-cyano-3-phenoxybenzyl (1RS,3RS)-(1RS,3RS)-3-(2,2,-dichlorovinyl)-2,2-dimethylcyclopropanecarboxylate), permethrin (3-phenoxybenzyl (1RS,3RS)-(1RS,3RS)-3-(2,2-dichlorovinyl)-2,2-dimethylcyclopropanecarboxylate), cyhalothrin ((R,S)-alpha-cyano-3-phenoxybenzyl (Z)-(1RS,3RS)-3-(2-chloro-3,3,3-trifluoropropenyl)-2,2-dimethylcyclopropanecarboxylate), deltamethrin ((S)-alphacyano-m-phenoxybenzyl (1R,3R)-3-(2,2-dibromovinyl)-2-dimethylcyclopropanecarboxylate, cycloprothrin ((RS)-alphacyano-3-phenoxybenzyl (RS)-2,2-dichloro-1-(4-ethoxyphenyl)cyclopropanecarboxylate), etc.); thiadiazine derivatives (e.g. buprofezin (2-tert-butylimino-3-isopropyl-5-phenyl-1,3,5-triazin-4-one), etc.); nitroimidazolidine derivatives (e.g. imidacloprid (1-((6-chloro-3-pyridylmethyl)-N-nitroimidazolidin-2-ylideneamine), etc.); nereistoxin derivatives (e.g. cartap (S,S'-(2-dimethylaminotrimethylene) bis(thiocarbamate), thiocyclam (N,N-dimethyl-1,2,3-trithian-5-ylamine), bensultap (S,S'-2-dimethylaminotrimethylene di(benzenethiosulphonate), etc.); halogenated hydrocarbons (e.g. endosulfan (6,7,8,9,10,10-hexachloro-1,5,5a,6,9,9a-hexahydro-6,9-methano-2,4,3-benzodioxathiepin-3-oxide), gamma-BHC (1,2,3,4,5,6-hexachlorocyclohexane), etc.); benzoylphenylurea derivatives (e.g. chlorfluazuron (1-[3,5-dichloro-4-(3-chloro-5-trifluoromethylpyridin-2-yloxy)phenyl]-3-(2,6-difluorobenzoyl)urea), teflubenzuron (1-(3,5-dichloro-2,4-difluorophenyl)-3-(2,6-difluorobenzoyl)urea), flufenoxuron (1-[4-(2-chloro-4-trifluoromethylphenoxy)-2-fluorophenyl]-3-(2,6-difluorobenzoyl)urea, etc.); formamidine derivatives (e.g. amitraz (N,N'-[(methylimino)dimethylidyne]di-2,4-xylidine), chlordimeform (N'-(4-chloro-2-methylphenyl)-N,N-dimethylmethanimidamide), etc.).

The composition may be applied to insect pests by a conventional manner, of which typical examples are spreading, fuming, soil treatment, incorporation into food for domestic animals or poultry, etc. It is further noticeable that addition of the composition to sericulture food may lead to an increase of cocoons in number or thickening the cocoon layer.

The dosage of the pyrazole compound (I) as the active ingredient in an agricultural insect pesticidal composition is generally from about 1 to about 500 grams per hectare, preferably about 5 to 100 grams per hectare. When the composition is applied as an emulsifiable concentrate or a wettable powder, the concentration of the active ingredient is generally from about 0.0001 to about 500 ppm, preferably from about 0.02 to 100 ppm. In case of such formulation as granules, fine granules and dusts, the composition may be applied as such without diluting with water. As a sanitary insect pesticidal composition, the composition in the form of an emulsifiable concentrate, an emulsifiable concentrate or a wettable powder may be diluted with water in a concentration of the active ingredient being generally from about 1 to about 500 ppm and applied. In case of the formulation such as an oil spray, an aerosol, a fumigant, a bait or the like, it may be applied as such.

Said amounts and concentrations are not decisive and may vary depending on the kind of preparation, season for application, locus to be applied, mode of application, species of insect pests, degree of damages, etc.

Some practical embodiments of the composition according to the invention are illustratively shown in the following Formulation Examples wherein % and part(s) are by weight.

FORMULATION EXAMPLE 1

The pyrazole compound (I) (20 parts), an emulsifier (a mixture of polyoxyethylene styrylphenyl ether, polymer of polyoxyethylene styrylphenyl ether and alkylarylsulfonate) (20 parts) and xylene (60 parts) are mixed well to make a 20% emulsifiable concentrate.

FORMULATION EXAMPLE 2

The pyrazole compound (I) (20 parts), an emulsifier (sodium laurylsulfate) (5 parts) and diatomaceous earth (#300 mesh; 75 parts) are mixed well in a pulverizer to make a 20% wettable powder.

FORMULATION EXAMPLE 3

The pyrazole compound (I) (3 parts), acetone (20 parts) and talc (#300 mesh; 97 parts) are mixed well in a pulverizer, followed by removal of acetone by evaporation to make a 3% dust.

FORMULATION EXAMPLE 4

The pyrazole compound (I) (5 parts), a dispersing agent (calcium ligninsulfonate) (2 parts) and clay (93 parts) are mixed well, followed by addition of a small amount of water. The resultant mixture is kneaded and granulated by the aid of a granulator and dried to make 5% granules.

FORMULATION EXAMPLE 5

The pyrazole compound (I) (2 parts), a dispersing agent (calcium ligninsulfonate) (2 parts) and clay (96 parts) are mixed well, followed by addition of a small amount of water. The resultant mixture is kneaded and granulated by the aid of a fine granulator and dried to make 2% fine granules.

FORMULATION EXAMPLE 6

The pyrazole compound (I) (0.2 part), xylene (2 parts), dimethylformamide (2 parts) and lamp oil (95.8 parts) are mixed well to make an oil spray.

FORMULATION EXAMPLE 7

The pyrazole compound (I) (0.05 part), tetramethrin (N-(3,4,5,6-tetrahydrophthalimido)methylchrysanthemate) (0.2 part), resmethrin (5-benzyl-3-furylmethyl ($\pm$)-cis,trans-chrysanthemate) (0.05 part), xylene (7 parts) and deodorized lamp oil (42.7 parts) are mixed well and charged into an aerosol container. Upon attachment of a valve portion, a pressurizing agent (LPG) (50 parts) is charged through the valve to make an aerosol.

FORMULATION EXAMPLE 8

The pyrazole compound (I) (1 part) and sesame oil (3 parts) are mixed, and butyl hydroxyanisole (0.03 part), dehydroacetic acid (0.1 part), black sugar (10 parts), crystalline cellulose (30 parts) and potato starch (55.87 parts) are added thereto. The resultant mixture is uniformly mixed and pressurized with a load of 15 kg/cm$^2$ to make a toxic bait in tablets, each tablet having a weight of approx. 4 g and a diameter of 30 mm.

FORMULATION EXAMPLE 9

The pyrazole compound (I) (10 parts) is added to 40 parts of an aqueous solution containing polyvinyl alcohol (6 parts), and the mixture is stirred in a mixer. To the resultant dispersion, 40 parts of an aqueous solution containing xanthane gum (0.05 part) and aluminum magnesium silicate (0.1 part) is added, followed by addition of propylene glycol (10 parts). The mixture is gently stirred to give 10% flowable.

FORMULATION EXAMPLE 10

A solution of the pyrazole compound (I) (0.2 part), d-allethrin (2,2-dimethyl-3-(2-methyl-1-propenyl)cyclopropanecarboxylic acid 2-methyl-4-oxo-3-(2-propenyl)2-cyclopenten-1-yl ester) (0.2 part), d-phenothrin (2,2-dimethyl-3-(2-methyl-1-propenyl)cyclopropanecarboxylic acid (3-phenoxyphenyl)methyl ester) (0.2 part), xylene (5 parts), deodorized kerosene (3.4 parts) and an emulsifier ("ATMOS 300" ® manufactured by Atlas Chemical Co., Ltd.) (1 part) in distilled water (50 parts) is filled in an aerosol container. After provision of a valve, a propellant (liquefied petroleum gas) (40 parts) is filled through the valve under reduced pressure to give a water-based aerosol.

FORMULATION EXAMPLE 11

The pyrazole compound (I) (100 mg) is dissolved in an appropriate amount of acetone, and the resultant solution is impregnated with a porous ceramic plate (4.0×4.0×1.2 cm) to give a fumigant.

FORMULATION EXAMPLE 12

The pyrazole compound (I) (5 parts), fenpropathrin ((RS)-alpha-cyano-3-phenoxybenzyl 2,2,3,3,3-tetramethylcyclopropanecarboxylate) (15 parts), an emulsifier (a mixture of polyoxyethylene styrylpheyl ether, polymer of polyoxyethylene ether and alkylaryl sulfate) (20 parts) and xylene (60 parts) are mixed well to make an emulsifiable concentrate.

The following Test Examples present some typical test date indicating the excellent insect pesticidal activity of the pyrazole compound (I). The compounds used for comparision are shown in Table 1 below:

TABLE 1

| Compound No. | Structure | Remarks |
|---|---|---|
| (A) | $CH_3O$, $CH_3$, $CH_3$, $CH_3$ — $C(CH_2)_3CHCH_2CH=CHC=CHCOOCH(CH_3)_2$ with $CH_3$ branch | Known as "methoprene"; U.S. Pat. No. 3,904,662 |
| (B) | phenyl—O—phenyl—O—$(CH_2)_3$—pyridyl | Canadian patent 1,231,945; Compound No. 118 |
| (C) | phenyl—O—phenyl—O—$CH_2$—pyrazolyl(N-$CH_3$) | EP-A1-287959; Compound No. 14-1 |
| (D) | phenyl—O—phenyl—O—$CH_2CH_2$—N(pyrazole) | U.S. Pat. No. 4,943,586; Compound No. |
| (E) | 3-Cl-phenyl—O—phenyl—O—$CH_2CH_2$—N(pyrazole) | U.S. Pat. No. 4,943,586; Compound No. |
| (F) | phenyl—O—phenyl—O—$CH_2CH_2CH_2$—N(pyrazole) | Synthesized for comparison |
| (G) | 2,4-diCl-phenyl—O—phenyl—O—$CH_2CH_2CH_2$—N(pyrazole) | Synthesized for comparison |

TEST EXAMPLE 1

An emulsifiable concentrate prepared according to Formulation Example 1 was diluted with water to make a designed concentration. The dilution (0.7 ml) was added to 100 ml of distilled water. Last instar larvae of common mosquito (*Culex pipiens pallens*) were released therein and reared for 7 days until their emergence, and the concentration for 50% inhibition (IC$_{50}$) was examined. The results are shown in Table 2.

TABLE 2

| Test compound | IC$_{50}$ (ppm) |
| --- | --- |
| Pyrazole compound (I) | 0.000009 |
| (A) | 0.00018 |
| (B) | 0.00013 |
| (D) | 0.00023 |
| (F) | 0.0007 |

TEST EXAMPLE 2

Powdered animal feed (2 g) was thoroughly mixed with bran (14 g). An emulsifiable concentrate prepared according to Formulation Example 1 was diluted with water to a designed concentration, and the dilution was added to the above mixture. The resultant mixture was stirred well to make an artificial culture. Thirty larvae of housefly (*Musca domestica*) were reared therein until their pupation. The obtained pupae were placed into a plastic cup, and the concentration for 50% inhibition was examined in the same manner as in Test Example 1. The results are shown in Table 3.

TABLE 3

| Test compound | IC$_{50}$ (ppm) |
| --- | --- |
| Pyrazole compound (I) | 0.14 |
| (A) | 2.3 |
| (B) | >3 |
| (C) | >3 |
| (E) | 1.0 |
| (G) | 1.8 |

What is claimed is:
1. 1-{3-[4-(3,5-Difluorophenoxy)phenoxy]propyl}-pyrazole.
2. An insect pesticidal composition which comprises as an active ingredient the pyrazole compound according to claim 1 and an inert carrier or diluent.
3. A method for controlling insect pests which comprises applying an insect pesticidally effective amount of the pyrazole compound according to claim 1 to the insect pests or the locus where the insect pests propagate.

* * * * *